United States Patent
Saito

(10) Patent No.: US 6,221,885 B1
(45) Date of Patent: Apr. 24, 2001

(54) PESTICIDAL COMPOSITIONS

(75) Inventor: Shigeru Saito, Toyonaka (JP)

(73) Assignee: Sumitomo Chemical Company, Limited, Osaka-fu (JP)

(*) Notice: Subject to any disclaimer, the term of this patent is extended or adjusted under 35 U.S.C. 154(b) by 0 days.

(21) Appl. No.: 09/378,691

(22) Filed: Aug. 23, 1999

(30) Foreign Application Priority Data

Sep. 24, 1998 (JP) .................................................. 10-269797

(51) Int. Cl.⁷ ............................ A01N 43/40; A01N 47/10
(52) U.S. Cl. ........................................... 514/345; 514/477
(58) Field of Search ..................................... 514/345, 477

(56) References Cited

U.S. PATENT DOCUMENTS 5,922,880 * 7/1999 Sakamoto et al. .................... 546/296

FOREIGN PATENT DOCUMENTS 96 11909   4/1996 (WO) .

OTHER PUBLICATIONS

Tomlin, The Pesticide Manual Incorporation The Agrochemicals Handbook, 10th Ed. (1995) pp 23,24,679,680+ 982–984.*

* cited by examiner

Primary Examiner—Allen J. Robinson
(74) Attorney, Agent, or Firm—Birch, Stewart, Kolasch & Birch, LLP

(57) ABSTRACT

Pesticidal compositions containing as active ingredients 3,5-dichloro-1-(3,3-dichloro-2-propenyloxy)-4-[3-(5-trifluoromethylpyridin-2-yloxy)propoxy]benzene of the formula:

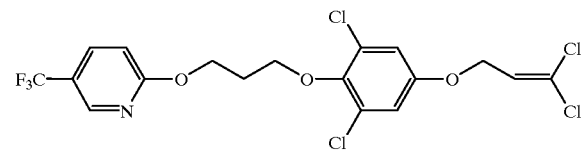

and at least one carbamate compound selected from thiodicarb, methomyl and alanycarb have excellent pesticidal activity by their synergistic cooperative action.

14 Claims, No Drawings

PESTICIDAL COMPOSITIONS

FIELD OF THE INVENTION

The present invention relates to pesticidal compositions.

BACKGROUND OF THE INVENTION

Various carbamate compounds have been used as active ingredients of pesticidal compositions; however, not all of them can exhibit satisfactory pesticidal effects and the occurrence of pests resistant to these carbamate compounds has been observed. For this reason, there has been a demand for the development of more effective pesticidal compositions.

SUMMARY OF THE INVENTION

Under these circumstances, the present inventors have extensively studied. As a result, they have found that pesticidal compositions containing as active ingredients 3,5-dichloro-1-(3,3-dichloro-2-propenyloxy)-4-[3-(5-trifluoromethylpyridin-2-yloxy)propoxy]benzene of the formula:

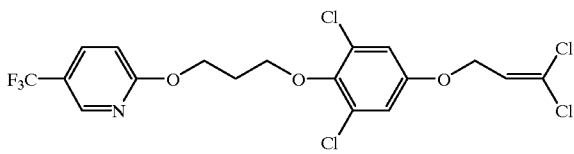

and at least one carbamate compound selected from thiodicarb, methomyl and alanycarb have excellent pesticidal activity and can attain the effective control of pest species which cannot be satisfactorily controlled by thiodicarb, methomyl or alanycarb and pest species which have acquired resistance to thiodicarb, methomyl or alanycarb, and further that their cooperative action is synergistic and therefore the application amount of thiodicarb, methomyl or alanycarb can be reduced as well as the development of resistance to thiodicarb, methomyl or alanycarb in various pests can be inhibited, thereby completing the present invention.

Thus, the present invention provides pesticidal compositions which comprise as active ingredients 3,5-dichloro-1-(3,3-dichloro-2-propenyloxy)-4-[3-(5-trifluoromethylpyridin-2-yloxy)propoxy]benzene (hereinafter referred to as compound A) and at least one carbamate compound selected from thiodicarb, methomyl and alanycarb (wherein the pesticidal compositions are hereinafter referred to as the present compositions).

DETAILED DESCRIPTION OF THE INVENTION

Compound A is disclosed in WO 96/11909 and can be prepared by the process described therein.

The carbamate compounds used in the present invention are specific ones each having a methyl(1-methylthioethylideneaminooxycarbonyl)amino group. Thiodicarb, methomyl and alanycarb are well known compounds as described in "The Pesticide Manual 10$^{th}$ Ed" (published by the British Crop Protection Council) on pages 982–984, 679–680 and 23–24, respectively. In the present invention, these commercially available compounds can be used. These carbamate compounds can also be produced according to the ordinary methods.

The pests against which the present compositions exhibit control activity may include, for example, arthropods such as insects and acarians, as recited below:

Hemiptera:

Delphacidae such as *Laodelphax striatellus, Nilaparvata lugens* and *Sogatella furcifera*; Deltocephalidae such as *Nephotettix cincticeps* and *Empoasca onukii*; Aphididae such as *Aphis gossypii* and *Myzus persicae*; Pentatomidae; Aleyrodidae such as *Trialeurodes vaporariorum, Bemisia tabaci* and *Bemisia argentifolii*; Coccidae; Tingidae; Psyllidae, etc.

Lepidoptera:

Pyralidae such as *Chilo suppressalis, Cnaphalocrocis medinalis, Ostrinia nubilalis* and *Parapediasia teterrella*; Noctuidae such as *Spodoptera litura, Spodoptera exigua, Pseudaletia separata, Mamestra brassicae, Agrotis ipsilon,* Trichoplusia spp., Heliothis spp., Helicoverpa spp. and Earias spp.; Pieridae such as *Pieris rapae crucivora*; Tortricidae such as *Adoxophyes orana fasciata, Grapholita molesta* and *Cydia pomonella*; Carposinidae such as *Carposina niponensis*; Lyonetiidae such as *Lyonetia clerkella*; Gracillariidae such as *Phyllonorycter ringoniella*; Phyllocnistidae such as *Phyllocnistis citrella*; Yponomeutidae such as *Plutella xylostella*; Gelechiidae such as *Pectinophora gossypiella*; Arctiidae; Tineidae, etc.

Diptera:

Calicidae, Aedes spp., Anopheles spp., Chironomidae, Muscidae, Calliphoridae, Sarcophagidae, Anthomyiidae, Cecidomyiidae, Agromyzidae, Tephritidae, Drosophilidae, Psychodidae, Simuliidae, Tabanidae, Stomoxyidae, etc.

Coleoptera:

Chrysomelidae, Scarabaeidae, Curculionidae, Attelabidae, Coccinellidae, Cerambycidae, Tenebrionidae, etc.

Thysanoptera:

Thripidae such as Thrips spp., e.g., *Thrips palmi*, Frankliniella spp., e.g., *Frankliniella occidentalis*, Sciltothrips spp., e.g., *Sciltothrips dorsalis*; and Phlaeotheripidae, etc.

Hymenoptera:

Tenthredinidae, Formicidae, Vespidae, etc.

Dictyoptera:

Blattidae, Blattellidae, etc.

Orthoptera:

Acrididae, Gryllotalpidae, etc.

Aphaniptera:

*Purex irritans* etc.

Anoplura:

*Pediculus humanus capitis* etc.

Isoptera:

Termitidae etc.

Acarina:

Tetranychidae such as Tetranychus spp. and Panonychus spp.; Tarsonemidae; Eriophyidae: Acaridae; Ixodioae, etc.

In the present compositions, the mixing ratio of compound A and the carbamate compound is usually in the range of 0.5: 99.5 to 60: 40 by weight, preferably 0.5: 99.5 to 50: 50 by weight. In particular, when the carbamate compound is methomyl or alanycarb, the mixing ratio is in the range of 0.5: 99.5 to 30: 70 by weight, more preferably 0.5: 99.5 to 20: 80 by weight. When the carbamate compound is thiodicarb, the mixing ratio is in the range of 1: 99 to 50: 50, more preferably 10: 90 to 50: 50 by weight.

The present compositions, although they may contain no other ingredients and may consist of compound A and the carbamate compound(s), can usually further contain solid carriers, liquid carriers, gaseous carriers or baits, and, if necessary, surfactants and other auxiliaries, and can take various forms of formulations, such as oil sprays, emulsifiable concentrates, wettable powders, flowables, granules, dusts, aerosols, fumigants (e.g., foggings), poison baits or microcapsule preparations.

These formulations usually contain as active ingredients compound A and at least one carbamate compound selected from thiodicarb, methomyl and alanycarb in the total amount of 0.01 to 95 wt. % for each formulation.

The solid carrier which can be used in the formulation may include, for example, fine powder or granules of clay materials such as kaolin clay, bentonite, Fubasami clay and acid clay; diatomaceous earth, synthetic hydrated silicon oxide, various kinds of talc, ceramics, and other inorganic minerals such as sericite, quartz, sulfur, activated carbon, calcium carbonate and hydrated silica; and chemical fertilizers such as ammonium sulfate, ammonium phosphate, ammonium nitrate, urea and ammonium chloride.

The liquid carrier may include, for example, water; alcohols such as methanol and ethanol; ketones such as acetone and methyl ethyl ketone; hydrocarbons such as hexane, cyclohexane, kerosene and light oil; esters such as ethyl acetate and butyl acetate; nitrites such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

The gaseous carrier or propellant may include, for example, Freon gas, butane gas, LPG (liquefied petroleum gas), dimethyl ether, and carbon dioxide.

The surfactant may include, for example, alkyl sulfates, alkyl sulfonates, alkyl arylsulfonates, alkyl aryl ethers and their polyoxyethylene derivatives, polyethylene glycol ethers, polyhydric alcohol esters, and sugar alcohol derivatives.

The auxiliaries such as fixing agents or dispersing agents may include, for example, casein, gelatin, polysaccharides such as powdered starch, gum arabic, cellulose derivatives and alginic acid; lignin derivatives, bentonite, sugars, and synthetic water-soluble polymers such as polyvinyl alcohol, polyvinyl pyrrolidone and polyacrylic acid.

The stabilizer may include, for example, PAP (isopropyl acid phosphate), BHT (2,6-di-tert-butyl-4-methylphenol), BHA (mixtures of 2-tert-butyl-4-methoxyphenol and 3-tert-butyl-4-methoxyphenol), vegetable oils, mineral oils, surfactants, fatty acids, and their esters.

The base material for used in poison baits may include, for example, bait materials such as grain powder, vegetable oils, sugars and crystalline cellulose; antioxidants such as dibutylhydroxytoluene and nordihydroguaiaretic acid; preservatives such as dehydroacetic acid; substances for preventing erroneous eating, such as red pepper powder; and attractant flavors such as cheese flavor and onion flavor.

The present compositions can also be prepared by separately formulating the active ingredients according to the above formulation technique, and then mixing these formulations with each other.

The present compositions thus formulated may be used as such or after diluted with water or other diluents. It may also be used in admixture with, or separately but simultaneously with, other insecticides, nematocides, acaricides, bactericides, fungicides, herbicides, plant growth regulators, synergists, fertilizers, soil conditioners and/or animal feeds.

When the present compositions are used as pesticidal compositions for agriculture, the application amounts are usually in the range of 1 to 100 g per hectare. In the case of emulsifiable concentrates, wettable powders, flowables, microcapsule preparations or similar formulations, which are used after diluted with water, the application concentrations are usually in the range of 1 to 10,000 ppm. In the case of granules, dusts or similar formulations, they are applied as such formulations without any dilution. When the present compositions are used as pesticidal compositions for epidemic prevention, they are usually applied after diluted with water to a concentration of 0.1 to 500 ppm in the case of emulsifiable concentrates, wettable powders, flowables, microcapsule preparations or similar formulations; or they are applied as such in the case of oil sprays, aerosols, fumigants, poisonous baits or similar formulations.

The application amount and concentration may vary depending upon the conditions including types of formulations, times, places and methods of application, kinds of pests, and degree of damage, and they can be increased or decreased without limitation to the above range.

EXAMPLES

The present invention will be further illustrated by the following Formulation Examples and Test Examples; however, the present invention is not limited to these Examples.

The following are Formulation Examples, where parts are by weight.

Formulation Example 1

First, 1 part of compound A and 10 parts of methomyl or alanycarb are dissolved in 36.5 parts of xylene and 36.5 parts of dimethylformamide, to which 10 parts of polyoxyethylene styryl phenyl ether and 6 parts of calcium dodecylbenzenesulfonate are added, and the mixture is well stirred to give an emulsifiable concentrate.

Formulation Example 2

First, 5 parts of compound A and 45 parts of methomyl or alanycarb are added to a mixture of 4 parts of sodium laurylsulfate, 2 parts of calcium lignin sulfonate, 22 parts of synthetic hydrated silicon oxide fine powder and 22 parts of diatomaceous earth, and the mixture is well stirred to give a wettable powder.

Formulation Example 3

To 1 part of compound A and 5 parts of methomyl or alanycarb are added 5 parts of synthetic hydrated silicon oxide fine powder, 5 parts of sodium dodecylbenzenesulfonate, 30 parts of bentonite and 54 parts of clay, and the mixture is well stirred. A suitable amount of water is added to the mixture, which is further stirred, granulated with a granulator, and air-dried to give a granule.

Formulation Example 4

First, 0.5 part of compound A, 4 parts of methomyl or alanycarb, 1 part of synthetic hydrated silicon oxide fine powder, 1 part of driless B (binder available from Sankyo Co., Ltd.) and 7 parts of clay are well mixed in a mortar and then stirred with a mixer. To the mixture is added 86.5 parts of cut-clay, and the mixture is well stirred to give a dust.

Formulation Example 5

First, 1 part of compound A, 10 parts of methomyl or alanycarb and 1.5 parts of sorbitan trioleate are mixed with 26 parts of an aqueous solution containing 2 parts of polyvinyl alcohol. The mixture is pulverized into fine particles with a particle size of not more than 3 μm with a sand grinder, to which 48 parts of an aqueous solution containing 0.05 part of xanthan gum and 0.1 part of aluminum magnesium silicate is added and 15 parts of propylene glycol is then added. The mixture is stirred to give a flowable.

Formulation Example 6

First, 0.1 part of compound A and 0.8 part of methomyl or alanycarb are dissolved in 5 parts of xylene and 5 parts of trichloroethane. The solution is mixed with 89.1 parts of deodorized kerosine to give an oil spray.

Formulation Example 7

First, 0.5 part of compound A, 4 parts of methomyl or alanycarb, 10 parts of trichloroethane and 55.5 parts of deodorized kerosine are mixed to make a solution. The solution is put in an aerosol vessel. The vessel is equipped with a valve, through which 30 parts of a propellant (liquefied petroleum gas) is charged under increased pressure to give an oil-based aerosol.

Formulation Example 8

An aerosol vessel is filled with a mixture of 0.1 part of compound A, 0.8 part of methomyl or alanycarb, 5 parts of xylene, 4.1 parts of deodorized kerosine and 1 part of Atmos 300 (surfactant available from Atlas Chemical Co.), as well as 50 parts of pure water. The vessel is equipped with a valve, through which 40 parts of a propellant (liquefied petroleum gas) are charged under increased pressure to give a water-based aerosol.

Formulation Example 9

First, 5 parts of compound A and 5 parts of thiodicarb are added to a mixture of 4 parts of sodium laurylsulfate, 2 parts of calcium lignin sulfonate, 42 parts of synthetic hydrated silicon oxide fine powder and 42 parts of diatomaceous earth, and the mixture is well stirred to give a wettable powder.

Formulation Example 10

First, 5 part of compound A, 5 parts of thiodicarb and 1.5 parts of sorbitan trioleate are mixed with 26 parts of an aqueous solution containing 2 parts of polyvinyl alcohol. The mixture is pulverized into fine particles with a particle size of not more than 3 μm with a sand grinder, to which 48 parts of an aqueous solution containing 0.05 part of xanthan gum and 0.1 part of aluminum magnesium silicate is added and 14.5 parts of propylene glycol is then added. The mixture is stirred to give a flowable.

Formulation Example 11

First, 0.3 parts of compound A and 45 parts of methomyl are added to a mixture of 4.7 parts of sodium laurylsulfate, 2 parts of calcium lignin sulfonate, 24 parts of synthetic hydrated silicon oxide fine powder and 24 parts of diatomaceous earth, and the mixture is well stirred to give a wettable powder.

The following shows by Test Examples that the present compositions exhibit excellent insecticidal effects.

Test Example 1

Insecticidal Test Against *Plutella xylostella* (pest line resistant to organic phosphorous agents, carbamate agents and other agents)

To an aqueous dilution of a test compound formulation obtained according to Formulation Example 1 was added New Rinou (spreading agent available from Nihon Nohyaku Co., Ltd.) to give a 3000-fold dilution. The resulting dilution was sprayed over potted cabbages (at the four to five leaf stage) at a volume of 25 ml per pot. The treated plants were air dried, and twenty third-instar larvae of *Plutella xylostella* were set free on each pot. After 5 days, the mortality was determined and the corrected mortality was calculated by the following equation:

Corrected mortality (%)=100×($Mt$−$Mc$)/(100−$Mc$)

where Mt and Mc are the mortalities (%) in the pots treated and untreated with the test compound, respectively.

The results are shown in Table 1.

TABLE 1

| Test compound | Application concentration (ppm) | Corrected mortality (%) |
|---|---|---|
| compound A | 1.56 | 0 |
| methomyl | 225 | 33 |
| compound A + methomyl | 1.56 + 225 | 80 |
| compound A | 1.56 | 22 |
| alanycarb | 200 | 0 |
| compound A + alanycarb | 1.56 + 200 | 83 |
| compound A | 3.13 | 33 |
| alanycarb | 200 | 0 |
| compound A + alanycarb | 3.13 + 200 | 100 |

Test Example 2

Insecticidal Test Against *Spodoptera litura*

To an aqueous dilution of a test compound formulation obtained according to Formulation Example 10 was added New Rinou (spreading agent available from Nihon Nohyaku Co., Ltd.) to give a 3000-fold dilution. The resulting dilution was sprayed over potted cabbages (at the four to five leaf stage) at a volume of 25 ml per pot. The treated plants were air dried, and ten fourth-instar larvae of *Spodoptera litura* were set free on each pot. After 4 days, the mortality was determined and the corrected mortality was calculated by the same equation as described in Test Example 1.

The results are shown in Table 2.

TABLE 2

| Test compound | Application concentration (ppm) | Corrected mortality (%) |
|---|---|---|
| compound A | 1.56 | 15 |
| thiodicarb | 1.56 | 44 |
| compound A + thiodicarb | 1.56 + 1.56 | 100 |

Test Example 3

Control Test Against *Helicoverpa armigera* on Cotton Plants

First, 10 parts of compound A was dissolved in 80 parts of Solvesso 150 (hydrocarbon solvent available from Exxon Chemical Company), to which 6 parts of Toximul 3454F (surfactant available from Stepan Company) and 4 parts of Toximul 3455F (surfactant available from Stepan Company) were added, and the mixture was well stirred to give an emulsifiable concentrate. An aqueous dilution of the emulsifiable concentrate was mixed with an aqueous dilution of a commercially available thiodicarb insecticide (trade name, Larvin 8ODF; available from Rhone Poulenc Ag Company) to have a prescribed concentration. The dilution was sprayed over cotton plants in each test field at a ratio of 450 L/ha by a power sprayer. One test field was 10 m×10 m in size, and each treatment was made in quadruplicate.

The evaluation of effects was based on the total number of parasitic larvae and the percent damage on cottonbolls in each treatment made in quadruplicate.

The results are shown in Tables 3 and 4.

TABLE 3

Parasitic larvae

| Test compound | Application amount (g test compd./ha) | Number of parasitic larvae before treatment | Number of parasitic larvae 7 days after treatment |
|---|---|---|---|
| compound A | 75 | 58 | 24 |
| thiodicarb | 900 | 64 | 10 |
| compound A + thiodicarb | 75 + 900 | 60 | 2 |
| no treatment | — | 63 | 59 |

TABLE 4

Protective effects (percent damage) on cottonbolls

| Test compound | Application amount (g test compd./ha) | Total number of cottonbolls 14 days after treatment | Damage on cottonbolls 14 days after treatment (%) |
|---|---|---|---|
| compound A | 75 | 538 | 8.1 |
| thiodicarb | 900 | 545 | 6.2 |
| compound A + thiodicarb | 75 + 900 | 648 | 0 |
| no treatment | — | 481 | 15.2 |

What is claimed is:

1. A pesticidal composition which comprises synergistically pesticidally effective amounts of 3,5-dichloro-1-(3,3-dichloro-2-propenyloxy)-4-(3-(5-trifluoromethylpyridin-2-yloxy)propoxy) benzene of the formula:

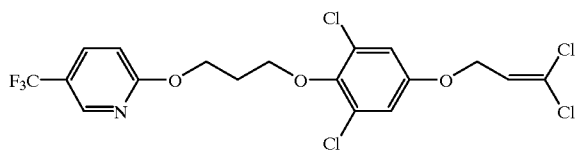

and at least one carbamate compound selected from thiodicarb, methomyl and alanycarb as active ingredients.

2. The pesticidal composition according to claim 1, wherein the mixing ratio of 3,5-dichloro-1-(3,3-dichloro-2-propenyloxy)-4-[3-(5-trifluoromethylpyridin-2-yloxy)propoxy]benzene and thiodicarb, methomyl or alanycarb is in the range of 0.5:99.5 to 50:50 by weight.

3. The pesticidal composition according to claim 1, wherein the carbamate compound is thiodicarb.

4. The pesticidal composition according to claim 1, wherein the carbamate compound is methomyl.

5. The pesticidal composition according to claim 1, wherein the carbamate compound is alanycarb.

6. The pesticidal composition according to claim 2, wherein the carbamate compound is methomyl or alanycarb and the mixing ratio is in the range of 0.5:99.5 to 20:80 by weight.

7. The pesticidal compound according to claim 2, wherein the carbamate compound is thiodicarb and the mixing ratio is in the range of 10:90 to 50:50 by weight.

8. A method for controlling pests, which comprises applying synergistically pesticidally effective amounts of 3,5-dichloro-1-(3,3-dichloro-2-propenyloxy)-4-(3-(5-trifluoromethylpyridin-2-yloxy)propoxy) benzene of the formula:

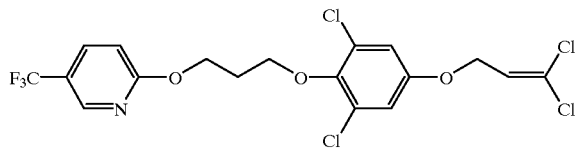

and at least one carbamate compound selected from thiodicarb, methomyl and alanycarb to pests or a locus where the pests inhabit.

9. The method according to claim 8, wherein 3,5-dichloro-1-(3,3-dichloro-2-propenyloxy)-4-[3-(5-trifluoromethylpyridin-2-yloxy)propoxy]-benzene and thiodicarb, methomyl or alanycarb is applied at a weight ratio of 0.5:99.5 to 50:50.

10. The method according to claim 8, wherein the carbamate compound is thiodicarb.

11. The method according to claim 8, wherein the carbamate compound is methomyl.

12. The method according to claim 8, wherein the carbamate compound is alanycarb.

13. The method according to claim 9, wherein the carbamate compound is methomyl or alanycarb and the mixing ratio is in the range of 0.5:99.5 to 20:80 by weight.

14. The method according to claim 9, wherein the carbamate compound is thiodicarb and the mixing ratio is in the range of 10:90 to 50:50 by weight.

* * * * *